United States Patent [19]

Finger

[11] Patent Number: Plant 5,888

[45] Date of Patent: Feb. 24, 1987

[54] KALANCHOE PLANT NAMED ATTRACTION

[75] Inventor: Hermann Finger, Wiesmoor, Fed. Rep. of Germany

[73] Assignee: Wiesmoor-Gartnerie und Baumschule GmbH, Fed. Rep. of Germany

[21] Appl. No.: 750,599

[22] Filed: Jul. 1, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A new and distinct Kalanchoe plant named Attraction, having abundant reddish orange flowers, compact growth habit with excellent branching, small and dense foliage, early flowering, and good keeping quality of its flowers.

1 Drawing Figure

1

The present invention relates to a new and distinctive cultivar of Kalanchoe plant, botanically known as *Kalanchoe blossfeldiana*, and referred to by the cultivar name Attraction.

Attraction was developed by me through controlled breeding by self-crossing the cultivar Java. Asexual reproduction of stem cuttings has shown that the unique features of this new Kalanchoe are stabilized and are reproduced true to type in successive propagations.

The following characteristics distinguish the new Kalanchoe from both its parent cultivars and other cultivated Kalanchoes of this type known and used in the floriculture industry:

1. Attraction is characterized by its high degree of self-branching, compact growth, and early flowering.

2. Branching is somewhat better than Pollux (disclosed in U.S. Plant Pat. No. 4,816), and much better than Cinnabar (disclosed in U.S. Plant Pat. No. 5,160).

3. Plant growth is compact like Pollux, with the cultivars Cinnabar and Inspiration being taller and not as dense. (Inspiration is disclosed in a pending application of the present inventor.)

4. Foliage is dense and small like Pollux, and not crenate like Cinnabar and Caliente.

5. Growth rate, leaf size, and self branching makes Attraction ideal for production in 10 cm pots.

6. After flower initiation plants must be treated with Alar in all seasons to reduce peduncle elongation.

7. Flowering time is 9 weeks in summer to 12 weeks in winter after start of short days. This is earlier than Pollux which is 11 weeks in summer and Inspiration which is 10 weeks in summer, but similar to Cinnabar.

8. Has well clustered flowers and a highly floriferous habit, with flowers that keep longer than Cinnabar.

9. The flower color is a reddish orange which is darker in color than Cinnabar but not as dark as Pollux or Inspiration.

10. Flower size and shape are similar to Pollus. Cinnabar is more pointed at the petal tip. The flower size of Attraction is larger than Inspiration.

The accompanying colored photograph illustrates the overall appearance of this cultivar taken as a perspective view of the plant and showing the colors as true as it is reasonably possible to obtain in a colored reproduction of this type.

The following is a detailed description of my new Kalanchoe cultivar based on plants produced under commercial practices in the greenhouses of Wiesmoor

2

Gartnerei in Wiesmoor, Germany. Color references are made to The Royal Horticultural Society Colour Chart except where general terms of ordinary dictionary significance are used.

Parentage: Controlled self of the cultivar Java.

Propagation:

(A) *Type cutting.*—Short stem cutting up to 2 cm long.

(B) *Time to root.*—10 days at 21° C. summer. 14 days at 21° C. winter.

(C) *Rooting habit.*—Many fine fibrous roots.

Plant description:

(A) *Form.*—Short, compact, best suited for growing and scheduling practices in 10 cm pots.

(B) *Habit of growth.*—Moderate rate of growth with excellent shoots formed generally at every node.

(C) *Foliage description.*—Leaves simple, opposite. (1) Size: Average full grown leaf of a flowering plant in a 10 cm pot is 110 mm long and 60 mm wide. (2) Shape: Ovate with obtuse apex and acute base. (3) Texture: Glabrous, coriaceous, succulent. (4) Margin: Dentate. (5) Color: Young foliage, top side 137B; under side 137C; Mature foliage, top side 137A; under side 137B.

Flowering description:

(A) *Flowering habits.*—Cyme inflorescence; each shoot is formed by dichotomous branching, starting with the opening of the terminal flower of the main axis, followed by terminal flowers of the side branching, continuing with subsequent development of branches in the inflorescence. Major inflorescence is 30 mm to 40 mm in diameter and lateral inflorescences are 20 mm to 30 mm in diameter.

(B) *Natural flowering season.*—Early January. Flowering time under controlled day length at 20° C. in summer is 9 weeks; in winter is 12 weeks. Flowering time depends on temperature, light intensity, and other growing conditions.

(C) *Flower buds.*—Elliptical to oblong and up to 12 mm long, developing to tubular as flower petals mature, sheathed with four green sepals; corolla at maturity is 10 mm long.

(D) *Flowers borne.*—On compound dichasial cymes; primary peduncle is 4 mm in diameter, with peduncle length depending on growing conditions and Alar application; pedicels up to 6 mm long.

(E) *Quantity of flowers.*—Highly floriferous, main axis has over 75 flowers and lateral branches have over 40 flowers, with six to eight side branches in a 10 cm pot.

(F) *Petals.*—(1) Shape: Nearly round, top cuspidate. (2) Color: Top when opening, 40A, fading to 40B; under side 41C–43C. (3) Number and Size of Petals: Four, united in corolla; petals 8 mm in diameter; flower 20 mm in diameter.

(G) *Reproductive organs.*—(1) Stamens: Eight in number. (a) Anther shape: Flat, elliptical; yellow in color. (b) Filament color: Light green. (c) Pollen color: Yellow. (2) Pistels: (a) Stigma: Flat shape, greenish white immature to white mature. (b) Style color: Light green. (c) Ovaries: Four-celled, 6 cm, green in color.

Disease resistance: Resistant to mildew. No other disease problems to date.

I claim:

1. A new and distinct cultivar of Kalanchoe named Attraction, as described and illustrated, and particularly characterized by its abundant reddish orange flowers, compact growth habit with excellent branching, small and dense foliage, early flowering, and by the good keeping quality of its flowers.

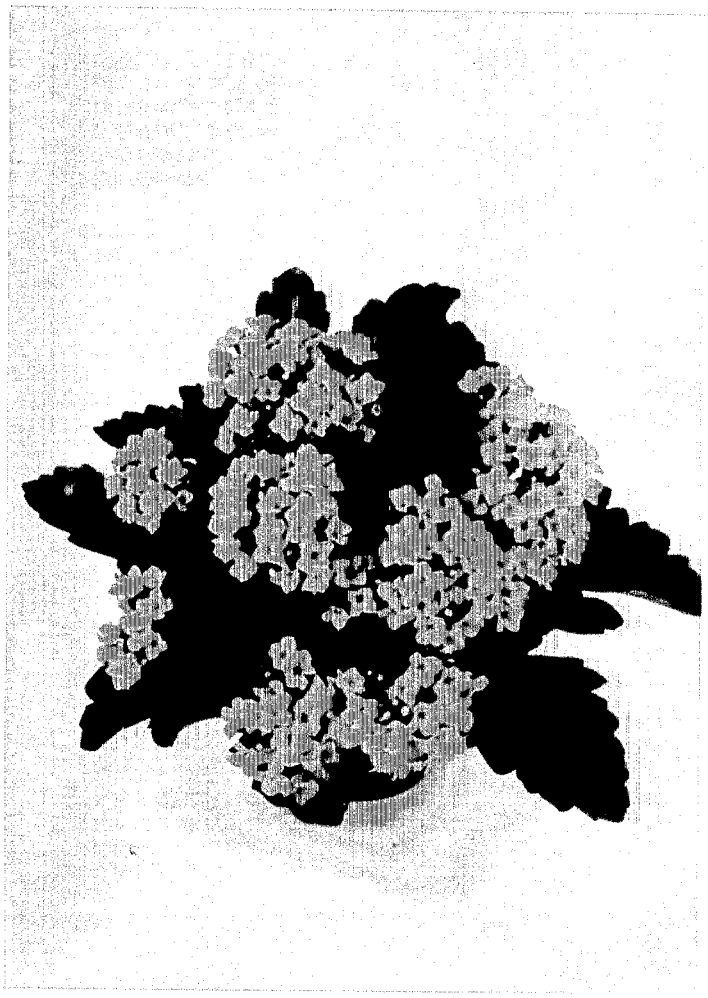

* * * * *